United States Patent [19]

Rogers et al.

[11] Patent Number: 5,405,323
[45] Date of Patent: Apr. 11, 1995

[54] CATHETER CHECK VALVE ASSEMBLY

[75] Inventors: Russell L. Rogers, Munith; Paul J. E. Fournier, Jackson; Gary B. Challender, Grass Lake, all of Mich.

[73] Assignee: Aeroquip Corporation, Maumee, Ohio

[21] Appl. No.: 199,713

[22] Filed: Feb. 22, 1994

[51] Int. Cl.$^6$ ............... A61M 31/00; A61M 5/178; A61M 5/00
[52] U.S. Cl. ................... 604/53; 604/167; 604/247; 604/249
[58] Field of Search ............... 604/49, 51–53, 604/89, 91, 164–169, 246, 247, 249, 256, 263, 198

[56] References Cited

U.S. PATENT DOCUMENTS

| | | | |
|---|---|---|---|
| 4,096,860 | 6/1978 | McLaughlin | 604/167 X |
| 4,430,073 | 2/1984 | Bemis et al. | 604/48 |
| 4,449,693 | 5/1984 | Gereg . | |
| 4,657,536 | 4/1987 | Dorman . | |
| 4,917,668 | 4/1990 | Haindl | 604/167 |
| 4,917,669 | 4/1990 | Bonaldo | 604/164 |
| 4,935,010 | 6/1990 | Cox et al. | 604/122 |
| 5,013,308 | 5/1991 | Sullivan et al. . | |
| 5,059,186 | 10/1991 | Yamamoto et al. | 604/280 |
| 5,062,836 | 11/1991 | Wendell | 604/167 |
| 5,069,663 | 12/1991 | Sussman . | |
| 5,073,168 | 12/1991 | Danforth . | |
| 5,090,424 | 2/1992 | Simon et al. . | |
| 5,108,380 | 4/1992 | Herlitze et al. | 604/283 |
| 5,112,301 | 5/1992 | Fenton, Jr. et al. . | |
| 5,156,596 | 10/1992 | Balbierz et al. | 604/164 |
| 5,156,600 | 10/1992 | Young . | |
| 5,167,636 | 12/1992 | Clement . | |
| 5,181,913 | 1/1993 | Erlich . | |
| 5,195,980 | 3/1993 | Catlin | 604/167 |
| 5,201,707 | 4/1993 | Kanai . | |
| 5,236,417 | 8/1993 | Wallis . | |
| 5,269,763 | 12/1993 | Boehmer et al. | 604/167 |

OTHER PUBLICATIONS

Publication by American National Standards Institute, Inc., "American National Standard for Medical Material-Luer Taper Fittings-Performance", ANSI/HIMA, MD70.1-1983, Revision of ANSI Z70.1-1955, copyright 1984.

Primary Examiner—John D. Yasko
Assistant Examiner—Adam J. Cermak
Attorney, Agent, or Firm—Emch, Schaffer, Schaub & Porcello Co.

[57] ABSTRACT

A catheter check valve assembly has a body member with a wall defining a generally cylindrical chamber and a transverse wall having an aperture lying on the axis of such chamber. A duckbill valve and an end cap supporting a catheter are positioned on one side of the transverse wall. A separator has a major portion positioned in said cylindrical chamber and an elongated cylindrical probe extending from said major portion. The separator is axially moveable from a retracted position where the probe is out of contact with the duckbill valve to a forward position extending through and opening the duckbill valve. A trocar may be extended through the catheter check valve assembly when the separator is in the forward position.

22 Claims, 4 Drawing Sheets

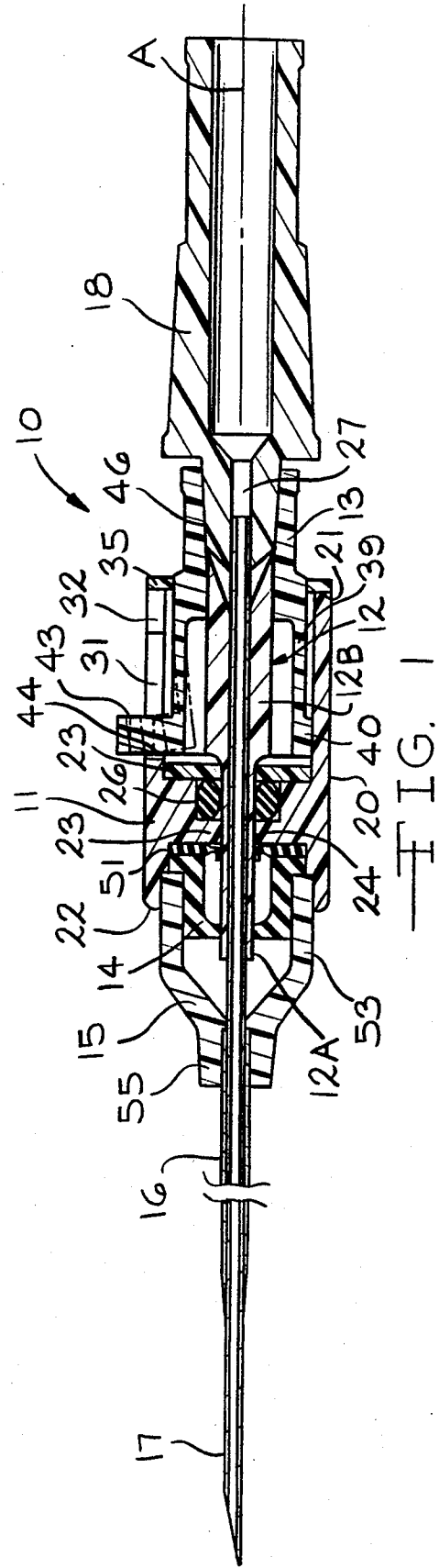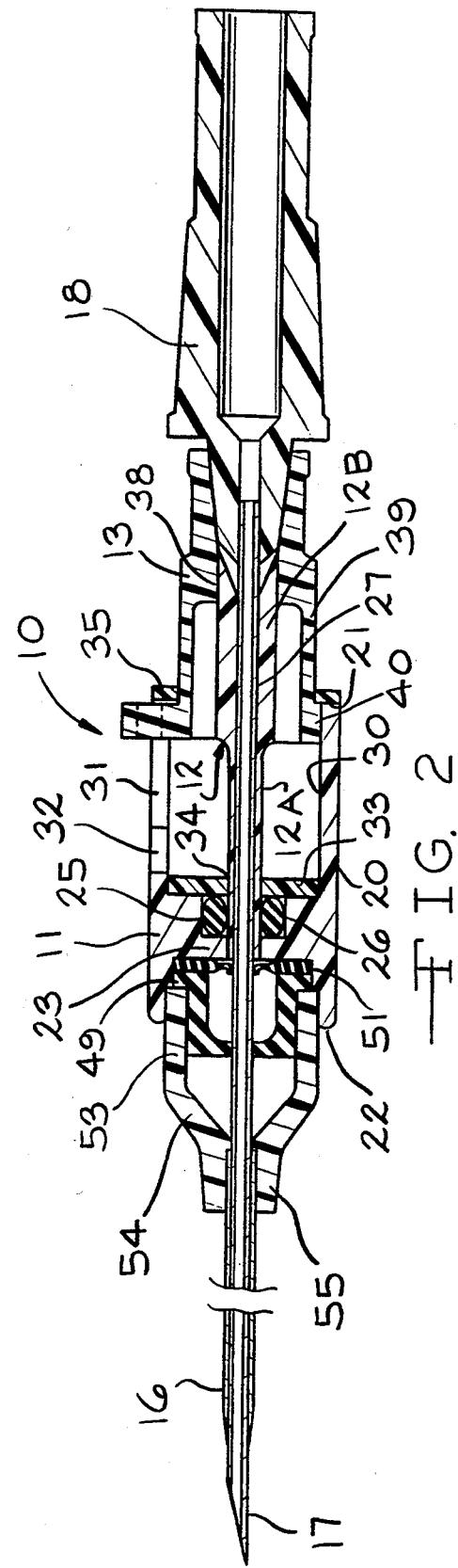

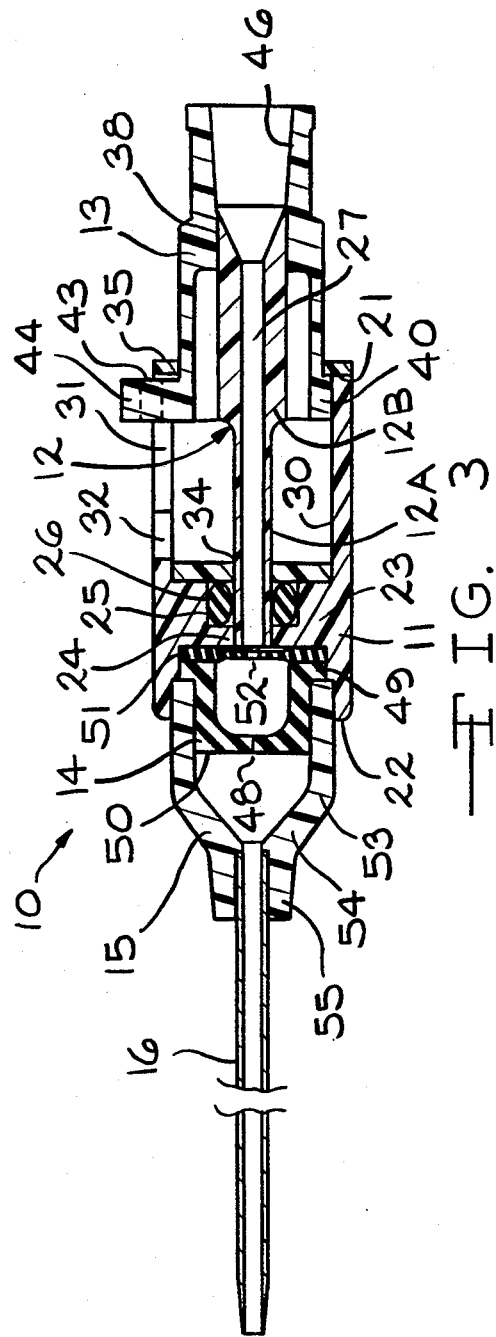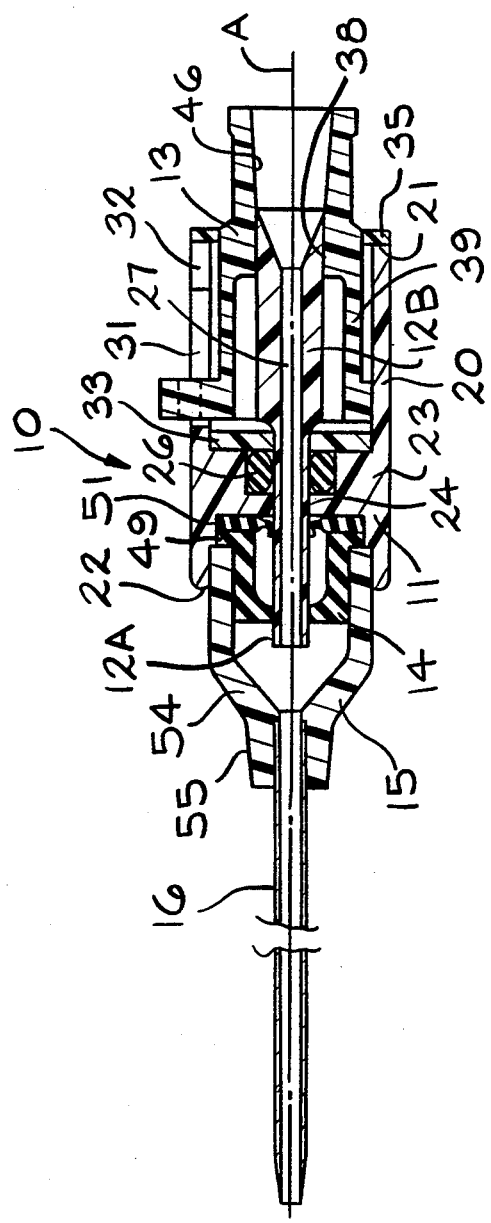

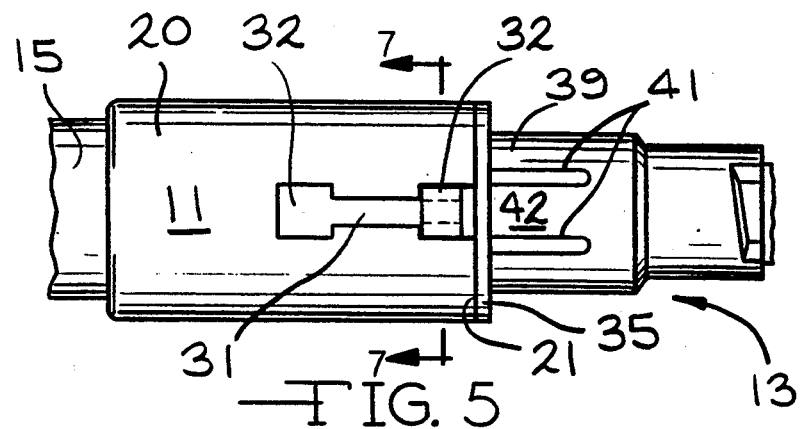
FIG. 5
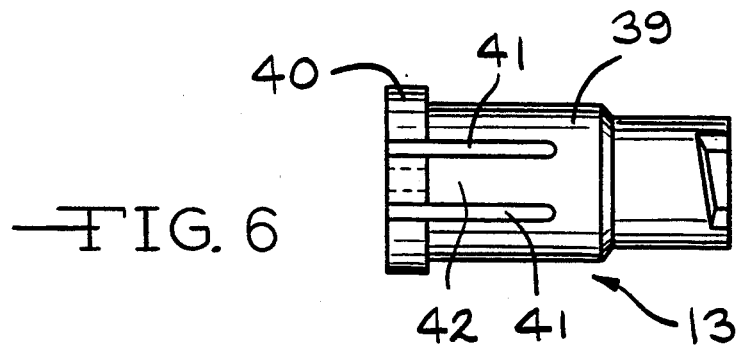
FIG. 6
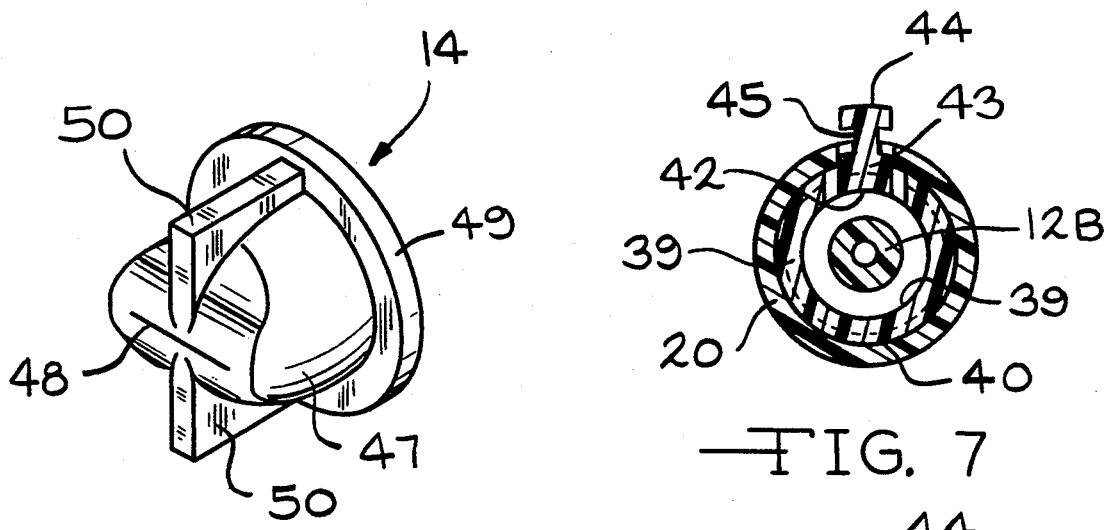
FIG. 9
FIG. 7
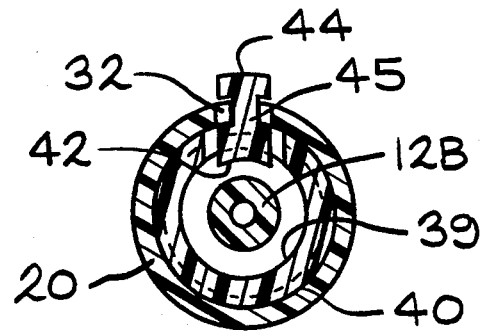
FIG. 8

CATHETER CHECK VALVE ASSEMBLY

BACKGROUND ART

The present invention relates to a catheter check valve assembly that prevents unintended back flow of body fluids through the catheter when the trocar used in placing the catheter in the body is removed. Body fluids may be withdrawn from the catheter check valve assembly while the catheter is inserted into the patient without the necessity of reinserting a trocar into the patient.

One significant problem with implanting a catheter in the bloodstream of a patient is the tendency of blood to squirt through the catheter during the implanting procedure, particularly upon removal of the trocar used in piercing the body for placement of the catheter therein.

An additional problem with prior art catheters used for transmitting fluids intervenously to a patient is that the patient frequently dislodges the intervenous feeding mechanism from the implanted catheter with the result that blood can then flow from the patient out of the catheter. Needless to say, any spillage or leakage of blood from the patient should be avoided if at all possible. The catheter check valve assembly of the present invention is designed such that, when in one operative position, blood or other bodily fluids may not flow from the body out of the catheter check valve assembly even if the intervenous fluid assembly mechanism inadvertently becomes detached therefrom and yet permits the intervenous fluid to be introduced into the patient while the catheter check valve assembly is in the same operative position.

Additionally, the catheter check valve assembly of the present invention, when moved to a different operative position, permits the withdrawal of blood or other bodily fluids therethrough without requiring reinsertion of a trocar. In other words, blood or other bodily fluids can be withdrawn from the patient directly through the catheter check valve assembly when such assembly is in a second operative position.

Accordingly, it is an object of the present invention to provide a catheter check valve assembly designed to avoid unintended spillage of blood or other bodily fluids while at the same time permitting, when in a different operative position, withdrawal of such blood or other bodily fluids directly therethrough.

A number of prior art patents show various types of catheter check valves. These include U.S. Pat. Nos. 4,449,693; 5,073,168; 5,112,301; 5,156,600 and 5,167,636.

DISCLOSURE OF INVENTION

The present invention provides a check valve assembly having a body member with a wall defining a generally cylindrical chamber and a transverse wall having an aperture lying on the axis of such chamber, a catheter and end cap extending from said body member with a duckbill valve positioned between the catheter and the transverse wall which duckbill valve, when closed, permits liquid to flow under pressure through the catheter check valve assembly but prevents liquid from flowing therethrough in the reverse direction. A separator having an elongated cylindrical probe with a passageway extending along the axis is axially moveable from a retracted position permitting the duckbill valve to close to an extended position opening the duckbill valve and opening communication in the reverse direction from the patient, through the catheter and the separator for withdrawing fluids from the patient.

BRIEF DESCRIPTION OF THE DRAWINGS

FIG. 1 is a sectional view taken along the longitudinal axis showing the catheter check valve assembly with a trocar supported on a male luer taper fitting extending therethrough and showing the separator in its extreme forward position.

FIG. 2 is a view similar to FIG. 1 showing the separator in its retracted position.

FIG. 3 is a view similar to FIG. 2 with the trocar and its luer fitting withdrawn from the catheter check valve assembly.

FIG. 4 is a view similar to FIG. 3 showing the separator moved to its forward position.

FIG. 5 is a fragmentary top plan view of the body and separator portion of the catheter check valve assembly.

FIG. 6 is a top plan view of the separator body.

FIG. 7 is a sectional view taken through line 7—7 of FIG. 5.

FIG. 8 is a view similar to FIG. 7 showing the tab in a depressed position preparatory to moving the separator from a retracted position to a forward position.

FIG. 9 is a perspective view of one type of duckbill valve which may be used as part of the catheter check valve assembly.

BEST MODE OF CARRYING OUT INVENTION

Figure 10:
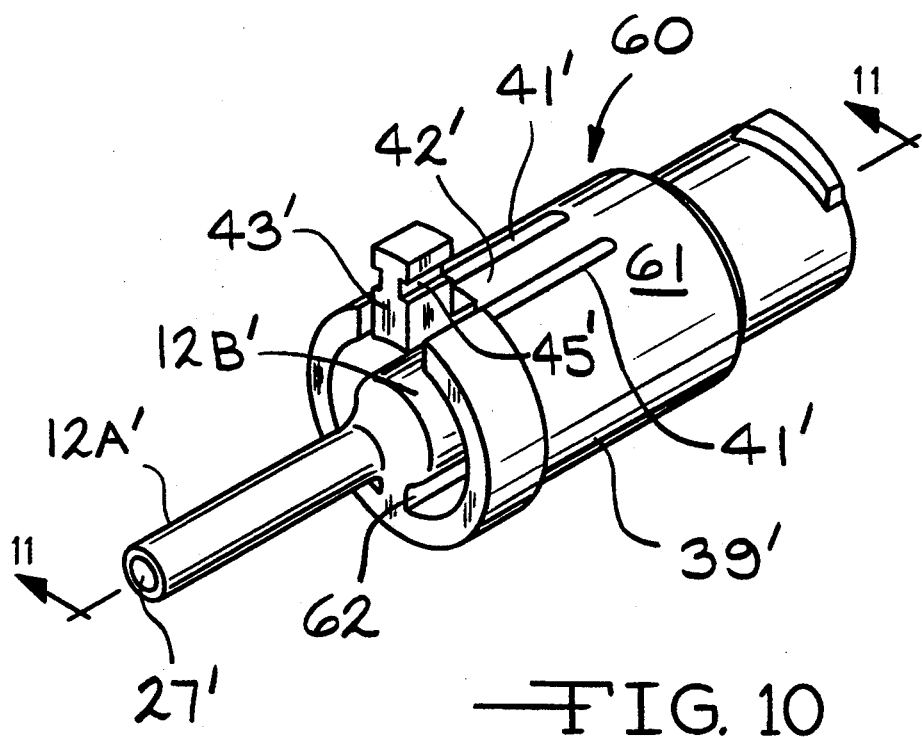
FIG. 10 is a perspective view of a modified, one-piece combined separator and separator body.

Referring now to FIGS. 1–8, there is shown one form of catheter check valve assembly 10. The assembly 10 includes a body member 11, a separator 12, a separator body 13, a duckbill valve 14 and an end cap 15 in which is mounted a catheter 16. FIGS. 1 and 2 also show a trocar 17 extending through the catheter check valve assembly 10 and supported on a male luer taper fitting 18 engaged to the catheter check valve assembly 10.

The body member 11 has a generally cylindrical wall 20 extending along an axis A from an inlet end 21 to an outlet end 22. A transverse wall 23 is positioned between the inlet end 21 and outlet end 22, significantly closer to the outlet end 22. The transverse wall 23 has an aperture 24 lying on axis A and an annular recess 25 on the inlet side in which is positioned an annular seal 26. The separator 12 includes (1) a tubular forward portion 12A, preferably cylindrical in shape and sized to extend through the aperture 24 and (2) a rearward portion 12B having a larger size, larger than the aperture 24 and, preferably, having a cylindrical exterior surface. The separator 12 has a passageway 27 extending therethrough and lying on axis A. The annular seal 26 is sized to sealingly engage the outer surface of the forward portion 12A of the separator 12.

The portion of the body member 11 between the inlet end 21 and the transverse wall 23 has a generally cylindrical interior surface 30. A longitudinal slot 31 is formed in the cylindrical wall 20 and extends generally parallel to the axis A from the inlet end 21 to a position slightly spaced from the transverse wall 23. The slot 31 has enlarged areas 32 at each end.

A disk 33 having an aperture 34 lying on axis A is frictionally or adhesively engaged to the cylindrical interior surface 30 in abutting relationship with the transverse wall 23 and functions to retain the annular seal 26 in position.

The separator body 13 includes a generally cylindrical wall member 39 having a radially extending flange 40 sized to slidingly engage the cylindrical interior surface 30 of the body member 11. The separator body 13 is positioned in the inlet end 21 of the body member 11 and is retained therein by a retaining ring 35 affixed to the cylindrical wall 20 at the inlet end 21 engaging the flange 40. The separator body 13 is adhesively or otherwise permanently affixed to the separator 12 at an area defining a cylindrical passageway 38 formed in the separator body 13 having a diameter sized to snugly receive the enlarged rearward portion 12B of the separator 12.

The cylindrical wall 39 has a pair of spaced apart slots 41 extending generally parallel to the axis A and parallel to each other. The slots 41 extend axially from an area of the cylindrical wall 39 slightly toward the outlet end from cylindrical passageway 38 to and through the radially extending flange 40 at the end of the separator body 13 facing the transverse wall 23. The longitudinal slots 41 cooperate to define a tab 42 retained as a cantilever on the separator body 13 and capable of being depressed inwardly toward the longitudinal axis A. Extending upwardly from the free end of the tab 42 is a post 43 terminating at its upper end in head 44 and having a central area 45 of reduced thickness in a direction laterally of the axis A.

The post 43, upon assembly of the separator body 13 to the body member 11, extends through the longitudinal slot 31 and is moveable therein as the separator body 13 carrying the separator 12 is moved from a retracted position shown in FIGS. 2, 3 and 5, to a forward position shown in FIGS. 1 and 4. Those portions of the post 43 above and below the central area 45 (as viewed in FIGS. 7 and 8) have a breadth greater than the width of the central portion of the longitudinal slot 31 but smaller than the width of the enlarged areas 32 at each end of the slot. When the separator body 13 is in the forward or retracted position, the post 43 is retained in one of the enlarged areas 32 so that the separator body 13 and the separator 12 carried thereby are retained in such forward or retracted position. When it is desired to move the separator body 13 from the retracted position to the forward position or from the forward position to the retracted position, the post 43 is depressed by pushing downwardly on the head 44 to move the tab 42 and the post 43 to a position at which the central area 45 of reduced breadth becomes aligned with the narrow central portion of slot 31 as shown in FIG. 8. Such alignment permits the separator body 13 and the separator 12 to be moved axially between a retracted and a forward position with the central area 45 moving through the slot 31 from one enlarged area 32 to the other.

The separator body 13 terminates in an outwardly flaring wall defining the female portion of a luer lock fitting 46 of the type set forth in American National Standard Institute No. ANSI/HIM MD70.1-983 which is incorporated herein by reference.

Positioned in the outlet end 22 of the body member 11 is the duckbill valve 14. One type of duckbill valve which may be utilized is one manufactured and sold by Vernay Laboratories, Inc., Yellow Springs, Ohio, as its Part No. VA-4518. The duckbill valve 14 has a radial flange 49 at its inlet end which is snugly received in the interior of the wall of the body member 11 extending between the transverse wall 23 and the outlet end 22.

The duckbill valve 14 has a cup 47 extending in an axial direction from the flange 49 with a closed end having a slit 48 extending across the axis A in one lateral direction and pair of ribs 50 extending in a lateral direction 90° to the slit 48. The ribs 50 thereby function as reinforcing members yieldingly urging the slit 48 to a closed position. A rubber disk 51 is positioned between the transverse wall 23 and the flange 49 of the duckbill valve 14. The rubber disk 51 has an aperture 52 lying on the axis A which is sized to sealingly engage a trocar extending therethrough but having sufficient resiliency to also stretch and sealingly engage the leading end 12A of the separator 12 when the separator is in its forward position.

The end cap 15 has a cylindrical wall portion 53 which is sealingly received in the inlet end 22 of body member 11 and positioned to clamp the radial flange 49 into sealing engagement with the rubber disk 51. Tapering inwardly and away from the cylindrical wall portion 53 is a tapered extension 54 and a nose 55 having a cylindrical passageway in which is mounted the catheter 16.

In operation, the catheter check valve assembly 10 has the separator 12 and separator body 13 moved to the forward position with the forward portion 12A of the separator 12 extending through the aperture 52 of the rubber disk 51 and through the slit 48 of duckbill valve 14. This permits the trocar 17 to be inserted through the passageway 27 without contacting either the disk 51 or the duckbill valve 14. Thereafter, the separator 12 is moved to the retracted position shown in FIG. 2 by pushing on the head 44 to depress the post 43 to a position at which the reduced thickness central area 45 is aligned with the longitudinal slot 31 thereby releasing the post 43 from the enlarged area 32 and permitting the retraction of the separator body 13 with the post 43 and the separator 12 position shown in FIG. 2. At that position, the trocar 17 extends a proper distance from the end of the catheter 16 for placement in the body of the patient. Upon placement in the body of the patient, the trocar 17 is removed by pulling the male luer taper fitting 18 out of engagement with the female portion of the luer lock fitting 46. The catheter check valve assembly 10 is now in a position permitting the introduction of intravenous fluids into a patient. In such position, the pressure from an elevated bottle of saline solution or other intravenous fluid will create sufficient pressure to open the slit 48 of the duckbill valve 14, thereby permitting such fluid to enter the patient. However, if the solution being introduced into the patient is inadvertently disconnected, blood may flow from the catheter 16 into the portion of the end cap 15 on the outlet side of the duckbill valve 14 but it will not be able to escape through the duckbill valve 14 as the slit 48 is urged to a closed position by the ribs 50.

At such time as it is desired to obtain a blood sample from the patient, it is necessary simply to disconnect the saline solution from the luer lock fitting 46 and then move the separator 12 and separator body 13 to the forward position shown in FIG. 4, thus opening the duckbill valve 14 and permitting blood sample to be removed through the passageway 27.

Figure 11:
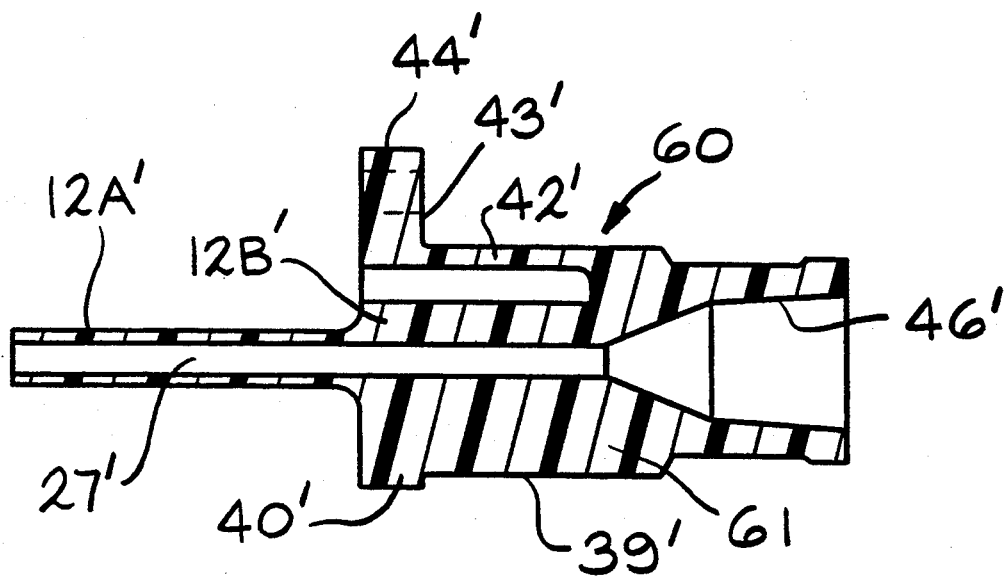
FIG. 11 is a sectional view taken through line 11—11 of FIG. 10.

Referring now to FIGS. 10 and 11, there is shown a modification in which the separator and separator body are formed as a single integrated unit generally designated by the numeral 60. Since many portions of the separator unit 60 are virtually identical to the joined separator 12 and separator body 13, they will be referred to using the same numerals as in the previous embodiment but followed by a prime sign.

The separator unit 60 includes an enlarged central portion 61 having an outer cylindrical wall 39′ with a tubular extension 12A′ extending axially from the central portion 61. Enlarged area 12B′ is joined to the cylindrical wall portion 39′ by a radially extending web 62. The cylindrical wall 39′ terminates at the leading end in a radial flange 40′. A pair of longitudinally extending slots 41′ define a tab 42′ having an upwardly extending post 43′ at the free end thereof. The post 43′ has an enlarged head 44′ and a central area 45′ of reduced thickness or breadth. The unit 60 has a central passageway 27′ and terminates at its inlet end with a female luer taper 46′. It operates in exactly the same manner as the embodiment of FIG. 2.

Many other modifications will become readily apparent to those skilled in the art. Accordingly, the scope of the present invention should be determined only by the scope of the appended claims.

We claim:

1. A catheter check valve assembly comprising:
   (a) a body member extending along an axis from first end to a second end, said body member having a longitudinal slot generally parallel to said axis;
   (b) a valve affixed to said body member first end, said valve, when in a first operative position permitting liquid flowing from said second end toward said first end, to flow therethrough but preventing the flow of liquid in the reverse direction and, when in a second operative position, permitting the flow of liquid therethrough in either direction; and
   (c) a separator having (i) a major portion including a forward end positioned in said body member second end for axial movement from a first position at which said forward end is closely adjacent said second end to a second position closer to said first end and (ii) a tubular probe extending along said axis from said major or portion and moveable therewith, said tubular probe, (A) when said forward end is in said first position, being disengaged from said valve to permit said valve to be maintained in said first operative position and, (B) when said forward end is moved to said second position, engaging said valve to move said valve to said second operative position, said separator being provided with an actuator positioned in said slot and axially movable therein upon axial movement of said separator.

2. The catheter check valve assembly of claim 1, wherein said slot is provided with a pair of spaced apart enlarged areas and said actuator includes a tab supported as a cantilever and extending to a free end yieldingly moveable toward and away from said axis, a post extending from said tab in the vicinity of said free end through said slot, said post configured to prevent axial movement of said separator when positioned in either of said enlarged areas and laterally away from said axis and to permit axial movement of said separator when positioned laterally toward said axis.

3. A catheter check valve assembly comprising:
   (a) a body member extending along an axis from first end to a second end, said body member having a longitudinal slot generally parallel to said axis;
   (b) a valve affixed to said body member first end, said valve, when in a first operative position permitting liquid flowing from said second end toward said first end, to flow therethrough but preventing the flow of liquid in the reverse direction and, when in a second operative position, permitting the flow of liquid therethrough in either direction;
   (c) an end cap housing said valve, said end cap engaged to said body member in the area of said first end and a catheter extending along said axis and supported on said end cap; and
   (d) a separator having (i) a major portion including a forward end positioned in said body member second end for axial movement from a first position at which said forward end is closely adjacent said second end to a second position closer to said first end and (ii) a tubular probe extending along said axis from said major portion and moveable therewith, said tubular probe, (A) when said forward end is in said first position, being disengaged from said valve to permit said valve to be maintained in said first operative position and, (B) when said forward end is moved to said second position engaging said valve to move said valve to said second operative position, said separator being provided with an actuator positioned in said slot and axially movable therein upon axial movement of said separator.

4. The catheter check valve assembly of claim 3, wherein said slot is provided with a pair of spaced apart enlarged areas and said actuator includes a tab supported as a cantilever and extending to a free end yieldingly moveable toward and away from said axis, a post extending from said tab in the vicinity of said free end through said slot, said post configured to prevent axial movement of said separator when positioned in either of said enlarged areas and laterally away from said axis and to permit axial movement of said separator when positioned laterally toward said axis.

5. A catheter check valve assembly comprising:
   (a) a body member extending along an axis from a first end to a second end, said body member being provided with a longitudinal slot generally parallel to said axis;
   (b) a valve affixed to said body member first end, said valve, when in a first operative position, permitting liquid flowing from said second end toward said first end, to flow therethrough but preventing the flow of liquid in the reverse direction and, when in a second operative position, permitting the flow of liquid therethrough in either direction;
   (c) an end cap housing said valve, said end cap engaged to said body member in the area of said first end and a catheter extending along said axis and supported on said end cap; and
   (d) a separator having (i) a major portion including a forward end positioned in said body member second end for axial movement from a first position at which said forward end is closely adjacent said second end to a second position closer to said first end, (ii) a tubular probe extending along said axis from said major portion and moveable therewith, said tubular probe, (A) when said forward end is in said first position being operatively disengaged from said valve to permit said valve to be maintained in said first operative position and, (B) when said forward end is moved to said second position, engaging said valve to move said valve to said second operative position and (iii) an actuator positioned in said slot moveable between a first position preventing axial movement of said separator and a second position permitting axial movement of said separator.

6. The catheter check valve assembly of claim 5, wherein said slot is provided with a pair of spaced apart enlarged areas and said actuator includes a tab supported as a cantilever and extending to a free end yieldingly moveable toward and away from said axis, a post extending from said tab in the vicinity of said free end through said slot, said post configured to prevent axial movement of said separator when positioned in either of said enlarged areas and laterally away from said axis and to permit axial movement of said separator when positioned laterally toward said axis.

7. A catheter check valve assembly comprising:
   (a) a body member extending along an axis from a first end to a second end, a transverse wall on said body member positioned between said first and second ends, said transverse wall having an aperture positioned on said axis, said body member having a longitudinal slot generally parallel to said axis;
   (b) an annular seal having a sealing aperture lying on said axis, said seal abutting said transverse wall between it and said first end;
   (c) a valve affixed to said body member first end, said valve, when in a first operative position, permitting liquid flowing from said aperture toward said first end, to flow therethrough but preventing the flow of liquid in the reverse direction through said valve and, when in a second operative position, permitting the flow of liquid therethrough in either direction; and
   (d) a separator having (i) a major portion including a forward end positioned in said body member second end for axial movement from a first position spaced from said transverse wall to a second position closer to said transverse wall and (ii) a tubular probe extending along said axis from said major portion and moveable therewith, said tubular probe, (A) when said forward end is in said first position, being disengaged from said valve to permit said valve to be maintained in said first operative position and, (B) when said forward end is moved to said second position, engaging said valve to move said valve to said second operative position, said sealing aperture sealingly engaging said tubular probe when said forward end is in said second position, said separator having an actuator positioned in said slot and axially moveable therein upon axial movement of said separator.

8. The catheter check valve assembly of claim 7, wherein said slot is provided with a pair of spaced apart enlarged areas and said actuator includes a tab supported as a cantilever and extending to a free end yieldingly moveable toward and away from said axis, a post extending from said tab in the vicinity of said free end through said slot, said post configured to prevent axial movement of said separator when positioned in either of said enlarged areas and laterally away from said axis and to permit axial movement of said separator when positioned laterally toward said axis.

9. A catheter check valve assembly comprising:
   (a) a body member extending along an axis from a first end to a second end, a transverse wall on said body member positioned between said first and second ends, said transverse wall having an aperture positioned on said axis, said body member having a longitudinal slot generally parallel to said axis;
   (b) an annular seal having a sealing aperture lying on said axis, said seal abutting said transverse wall between it and said first end;
   (c) an end cap housing said valve, said end cap engaged to said body member in the area of said first end and a catheter extending along said axis and supported on said end cap;
   (d) a valve affixed to said body member first end, said valve, when in a first operative position, permitting liquid flowing from said aperture toward said first end, to flow therethrough but preventing the flow of liquid in the reverse direction through said valve and, when in a second operative position, permitting the flow of liquid therethrough in either direction; and
   (e) a separator having (i) a major portion including a forward end positioned in said body member second end for axial movement from a first position spaced from said transverse wall to a second position closer to said transverse wall and (ii) a tubular probe extending along said axis from said major portion and moveable therewith, said tubular probe, (A) when said forward end is in said first position, being disengaged from said valve to permit said valve to be maintained in said first operative position and, (B) when said forward end is moved to said second position, engaging said valve to move said valve to said second operative position, said sealing aperture sealingly engaging said tubular probe when said forward end is in said second position, said separator having an actuator positioned in said slot and axially moveable therein upon axial movement of said separator.

10. The catheter check valve assembly of claim 9, wherein said slot is provided with a pair of spaced apart enlarged areas and said actuator includes a tab supported as a cantilever and extending to a free end yieldingly moveable toward and away from said axis, a post extending from said tab in the vicinity of said free end through said slot, said post configured to prevent axial movement of said separator when positioned in either of said enlarged areas and laterally away from said axis and to permit axial movement of said separator when positioned laterally toward said axis.

11. The catheter check valve assembly of claim 10, wherein said assembly is adapted to receive a trocar at said second end along said longitudinal axis for extension from said second end through said catheter.

12. A catheter check valve assembly comprising:
   (a) a body member extending along an axis from a first end to a second end, a transverse wall on said body member positioned between said first and second ends, said transverse wall having a first side facing said first end and second side facing said second end and having an aperture positioned on said axis, said body member being provided with a longitudinal slot generally parallel to said axis;
   (b) an annular seal having a sealing aperture lying on said axis, said seal abutting said transverse wall first side;
   (c) a valve affixed to said body member first end and engaged to said annular seal, said valve, when in a first operative position, permitting liquid flowing from said aperture toward said first end, to flow therethrough but preventing the flow of liquid in the reverse direction through said valve and, when in a second operative position, permitting the flow of liquid therethrough in either direction;

(d) an end cap housing said valve, said end cap engaged to said body member in the area of said first end and a catheter extending along said axis and supported on said end cap; and (e) a separator having (i) a major portion including a forward end positioned in said body member second end for axial movement from a first position spaced from said transverse wall to a second position closer to said transverse wall and (ii) a tubular probe extending along said axis from said major portion and moveable therewith, said tubular probe, (A) when said forward end is in said first position, being disengaged from said valve, said valve being maintained in said first operative position and, (B) when said forward end is moved to said second position, engaging said valve to move it to said second operative position, said sealing aperture sealingly engaging said tubular probe when said forward end is in said second position, and (iii) an actuator positioned in said slot moveable between a first position preventing axial movement of said separator and a second position permitting axial movement of said separator.

13. The catheter check valve assembly of claim 12, wherein said slot is provided with a pair of spaced apart enlarged areas and said actuator includes a tab supported as a cantilever and extending to a free end yieldingly moveable toward and away from said axis, a post extending from said tab in the vicinity of said free end through said slot, said post configured to prevent axial movement of said separator when positioned in either of said enlarged areas and laterally away from said axis and to permit axial movement of said separator when positioned laterally toward said axis.

14. The catheter check valve assembly of claim 12, wherein said assembly is adapted to receive a trocar at said second end along said longitudinal axis for extension from said second end through said catheter.

15. The catheter check valve assembly of claim 14, wherein said sealing aperture is sized to sealingly engage said trocar.

16. A catheter check valve assembly comprising
    (a) a body portion having (i) a cylindrical wall defining a passageway extending along an axis from a first end to a second end and (ii) a transverse wall between said first end and said second end, said transverse wall having an aperture lying on said axis and opposing sides facing, respectively, said first end and said second end;
    (b) a disc seal abutting said transverse wall side facing said first end, said disc seal having an aperture lying on said axis and a resilient annular seal encircling said aperture;
    (c) a duckbill valve having (i) an open end positioned in said body portion first end sealingly abutting said disc seal and (ii) a duckbill end extending therefrom, said duckbill end being yieldingly urged to a closed position;
    (d) an end cap having (i) an enlarged end portion engaged to said body portion first end and receiving said duckbill end therein and (ii) a nose portion extending from said enlarged end portion, said nose portion having a passageway extending along said axis;
    (e) a catheter retained on said nose portion and having a passageway extending axially from said nose portion; and
    (f) a separator engaged to said body portion, said separator including (i) a major portion including a forward end positioned in said body portion second end for axial movement from a first position spaced from said transverse wall to a second position closer to said transverse wall and (ii) a tubular probe extending along said axis from said major portion and moveable therewith, said tubular probe, (A) when said forward end is in said first position, being disengaged from said duckbill end, said duckbill end being maintained in said closed position and, (B) when said forward end is moved to said second position, extending through said duckbill end to open communication between said second end and said catheter.

17. The catheter check valve assembly of claim 16, wherein said body portion cylindrical wall is provided with a longitudinal slot between said second end and said transverse wall extending generally parallel to said axis and said separator is provided with an actuator positioned in said slot and axially moveable therein upon axial movement of said separator.

18. The catheter check valve assembly of claim 17, wherein said slot is provided with a pair of spaced apart enlarged areas and said actuator includes a tab supported as a cantilever and extending to a free end yieldingly moveable toward and away from said axis, a post extending from said tab in the vicinity of said free end through said slot, said post configured to prevent axial movement of said separator when positioned in either of said enlarged areas and laterally away from said axis and to permit axial movement of said separator when positioned laterally toward said axis.

19. A method of intravenously administering liquids to and removing bodily liquids from a living being comprising the steps of
    (a) providing a catheter check valve assembly having
        (i) a body member extending along an axis from a first end to a second end, a transverse wall on said body member positioned between said first and second ends, said transverse wall having an aperture positioned on said axis;
        (ii) a valve affixed to said body member first end, said valve, when in a first operative position, permitting liquid flowing from said aperture toward said first end, to flow therethrough but preventing the flow of liquid in the reverse direction through said valve and, when in a second operative position, permitting the flow of liquid therethrough in either direction;
        (iii) a separator having (1) a major portion including a forward end positioned in said body member for axial movement from a first position spaced from said transverse wall to a second position closer to said transverse wall and (2) a tubular probe extending along said axis from said major portion and moveable therewith, said tubular probe, (A) when said forward end is in said first position, being disengaged from said valve such that said valve is maintained in said first operative position and, (B) when said forward end is moved to said second position, engaging said valve to move it to said second operative position;

(iv) an end cap housing said valve, said end cap engaged to said body member in the area of said first end; and (v) a catheter extending along said axis and supported on said end cap;

(b) positioning said separator forward end in said second position;

(c) inserting a trocar having a pointed end through said separator, said end cap and said catheter to a position at which said pointed end extends beyond said catheter a predetermined distance;

(d) moving said separator forward end to said first position, said movement causing retraction of said trocar to a position at which said pointed end extends beyond said catheter a distance less than said predetermined distance;

(e) placing said trocar pointed end and said catheter in a patient; and (f) withdrawing said trocar from the patient while leaving said catheter in place.

20. The method of claim 19 further including the step of introducing liquids through said catheter check valve assembly including said catheter and into the patient while said separator forward end is in said first position.

21. The method of claim 19 further including the steps of moving said separator forward end to said second position and, thereafter, removing bodily fluids from the patient through said catheter and said separator.

22. The method of claim 21 further including the step of moving said separator forward end to said first position and permitting said valve to move from said second operative position to said first operative position.

* * * * *